US00PP19656P2

(12) United States Plant Patent
Hamilton et al.

(10) Patent No.: US PP19,656 P2
(45) Date of Patent: Jan. 20, 2009

(54) RASPBERRY PLANT NAMED 'DRISRASPONE'

(50) Latin Name: *Rubus ideas L.*
Varietal Denomination: DrisRaspOne

(75) Inventors: Brian K. Hamilton, San Jose, CA (US); Miguel H. Ahumada, Ojai, CA (US); Peter A. Martini, Marina, CA (US); Richard E. Harrison, Aptos, CA (US)

(73) Assignee: Driscoll Strawberry Associates, Inc., Watsonville, CA (US)

( * ) Notice: Subject to any disclaimer, the term of this patent is extended or adjusted under 35 U.S.C. 154(b) by 0 days.

(21) Appl. No.: 12/009,216

(22) Filed: Jan. 17, 2008

(51) Int. Cl.
*A01H 5/00* (2006.01)

(52) U.S. Cl. ..... Plt./204
(58) Field of Classification Search ..... Plt./204
See application file for complete search history.

*Primary Examiner*—Annette H Para
(74) *Attorney, Agent, or Firm*—Jondle & Associates, P.C.

(57) ABSTRACT

This invention relates to a new and distinct cultivar of raspberry plant named 'DrisRaspOne'. A new cultivar primarily characterized by its large plant size, high productivity with a long fruiting season, large fruit with a medium red color and a high percentage of titratable acidity is disclosed.

2 Drawing Sheets

Genus and species: *Rubus ideas L.*
Variety denomination: 'DrisRaspOne'.

BACKGROUND OF THE NEW PLANT

The present invention relates to a new and distinct raspberry cultivar designated 'DrisRaspOne' and botanically known as *Rubus ideas*. This new raspberry cultivar was discovered in Santa Cruz, Calif. September, 2002 and originated from a cross between the female parent 'T186.1' an unpatented proprietary raspberry plant and the male parent 'Driscoll Maravilla' (U.S. Plant Pat. No. 14,804). The original seedling of the new cultivar was asexually propagated at a nursery in Santa Cruz, Calif. 'DrisRaspOne' was subsequently asexually propagated and underwent further testing at a nursery in Santa Cruz, Calif. for five years. The present invention has been found to be stable and reproduce true to type through successive asexual propagations.

DESCRIPTION OF THE PHOTOGRAPHS

The accompanying color photographs show typical specimens of the new cultivar at various stages of development as nearly true as it is possible to make in color reproductions.

DESCRIPTION OF THE NEW CULTIVAR

Figure 1:
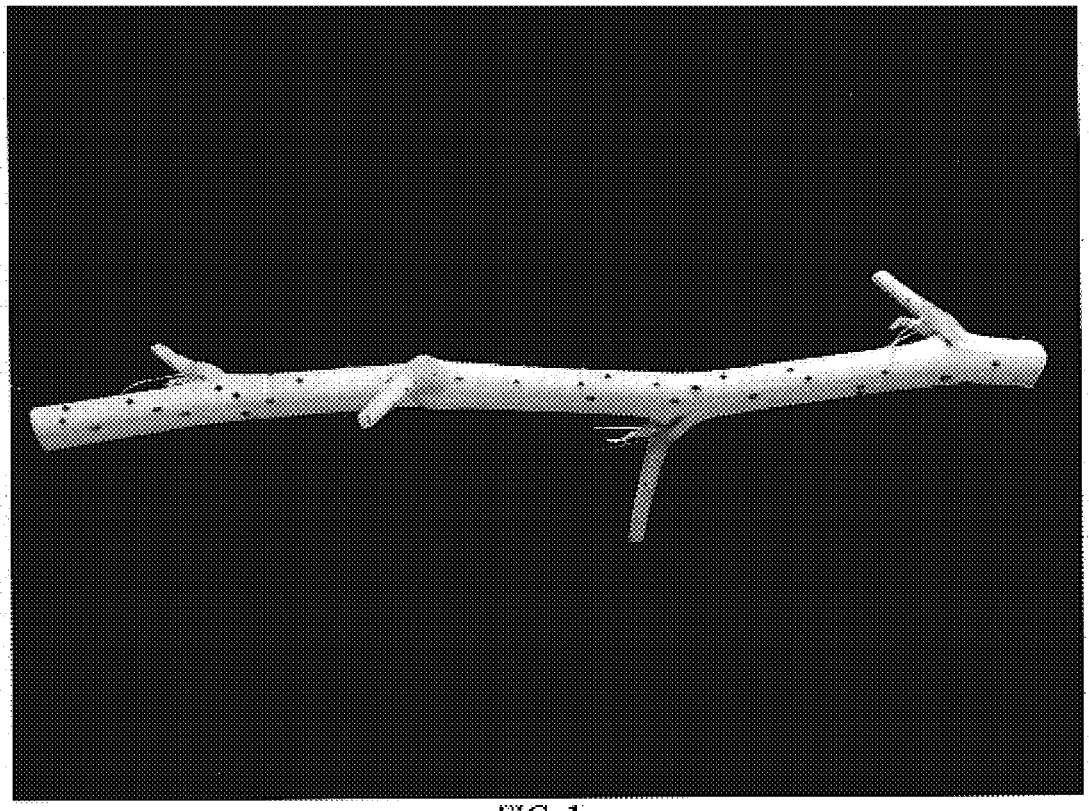
FIG. 1 shows a section of a young cane with prickles.
Figure 2:
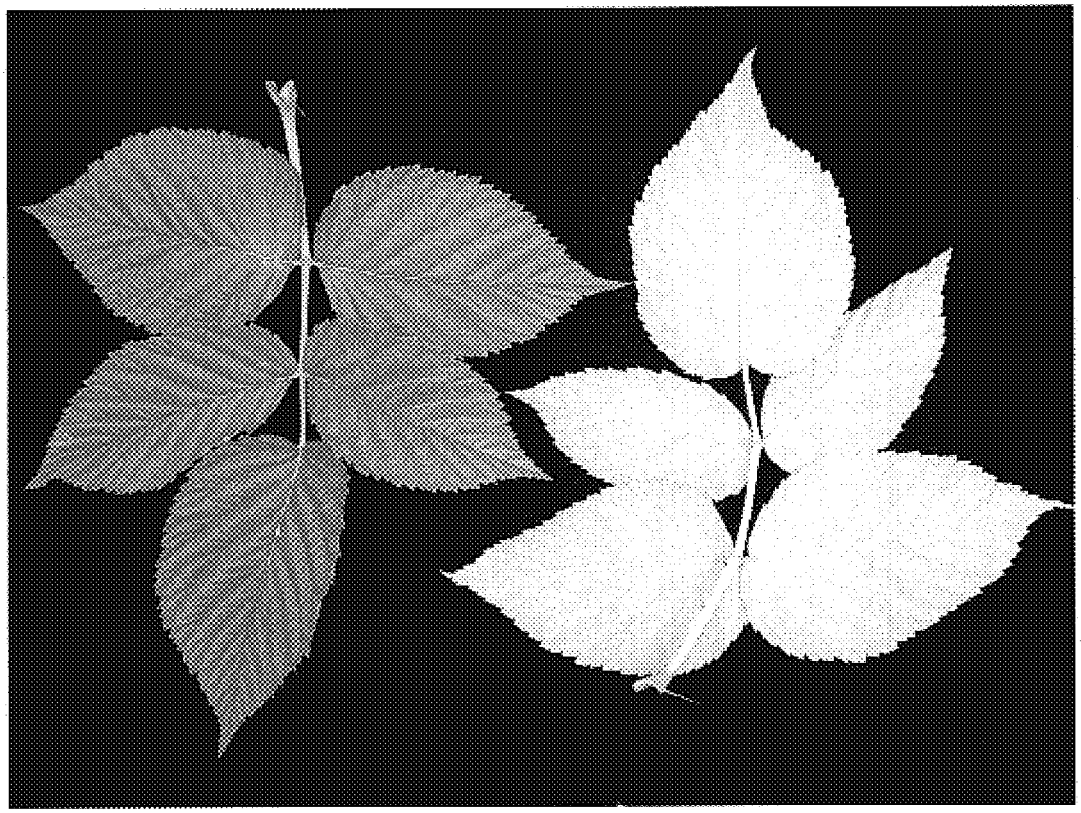
FIG. 2 shows both the upperside and underside of the plant leaves.
Figure 3:
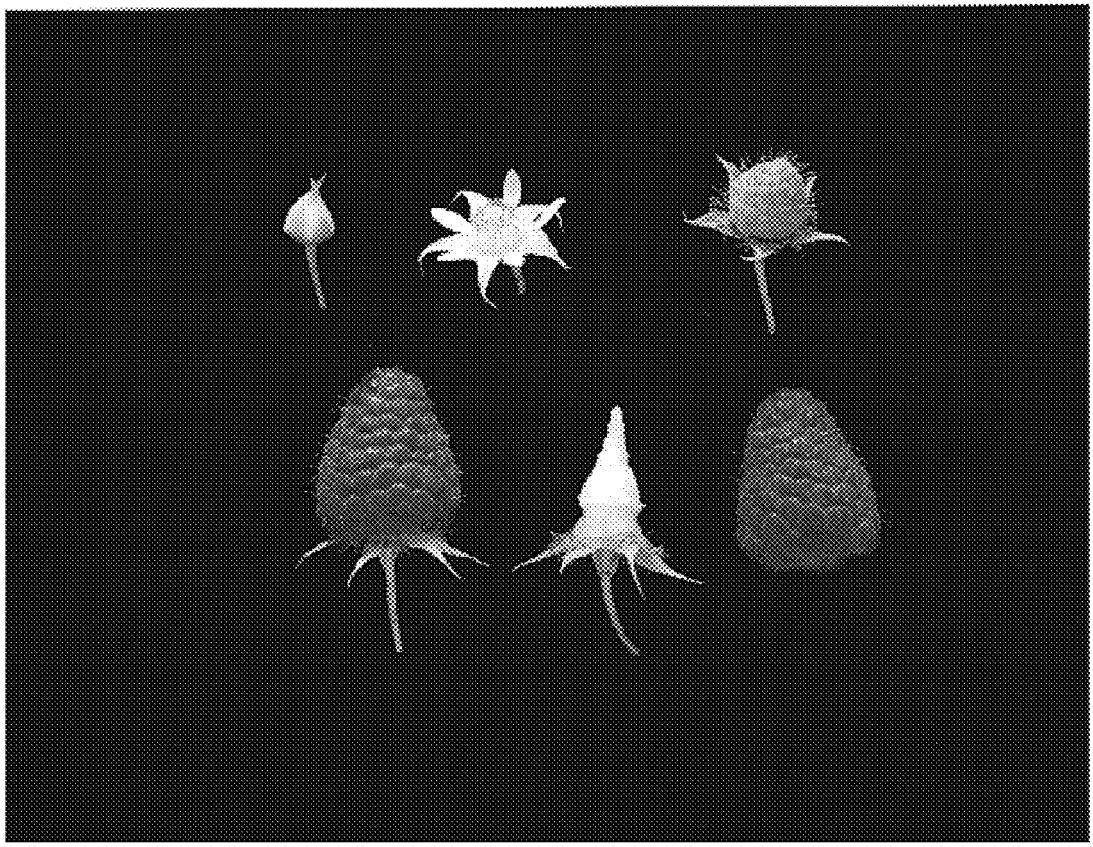
FIG. 3 shows a flower bud, a mature flower, an immature fruit, a mature fruit, a fruit plant and a mature fruit with out the fruit plug.

The following description of 'DrisRaspOne' is based on observations taken from the 2003 to 2007 growing seasons in Santa Cruz, Calif. This description is in accordance with UPOV terminology. Color designations, color descriptions, and other phenotypical descriptions may deviate from the stated values and descriptions depending upon variation in environmental, seasonal, climatic and cultural conditions. 'DrisRaspOne' has not been observed under all possible environmental conditions. Color terminology follows The Royal Horticultural Society Colour Chart, London (R.H.S.) (2001).

DETAILED BOTANICAL DESCRIPTION

Table 1 shows plant characteristics of the new variety compared with plant characteristics of the male parent 'Driscoll Maravilla', (U.S. Plant Patent 14,804). characteristics include terminal leaflet width, fruit glossiness, average fruit length in centimeters, average fruit width in centimeters and titratable acidity (percentage as citric acid).

TABLE 1

| Characteristic | 'DrisRaspOne' | 'Driscoll Maravilla' |
|---|---|---|
| Terminal leaflet width | 7.3 cm | 8.4 cm |
| Fruit glossiness | Strong | Medium |
| Average fruit length | 2.94 cm | 2.2 cm |
| Average fruit width | 2.70 cm | 2.2 cm |
| Titratable acidity (% as citric acid) | 15.3 | 8.5 |

Table 2 shows plant characteristics of the new variety compared with plant characteristics of the raspberry plant 'Heritage', (unpatented). Characteristics include plant size, plant productivity, primocane fruiting including cane length at end of first growing season in centimeters, dormant cane color, prickle length in centimeters (the average of 20 prickles measured 1 meter from ground at end of growing season from the base to the tip), prickle texture, petiole pigmentation of upper surface, terminal leaflet length in centimeters, lateral leaflet average length in centimeters, fruit color, average fruit length in centimeters and average fruit width in centimeters.

TABLE 2

| Characteristic | 'DrisRaspOne' | 'Heritage' |
|---|---|---|
| Plant size | Large | Medium |
| Plant productivity | High | Low |
| Primocane fruiting: cane length at end of first growing season | 219 cm | 204 cm |
| Dormant cane color | RHS 164B (Brown) | RHS 166C (Brown to purple) |
| Prickles: length (mean average of 20 measured 1 meter from ground at end of growing season-base of tip) | 0.16 cm | 0.22 cm |
| Prickles: Texture | Soft | Heavy |
| Petiole pigmentation of upper surface | RHS 144C (Light yellow-green) | RHS 183C (Dark greyed-purple) |
| Terminal leaflet length | 10.3 cm | 14.7 cm |
| Lateral leaflet average length | 9.6 cm | 13.4 cm |
| Fruit color | Medium red | Dark red |
| Average fruit length | 2.94 cm | 2.26 cm |
| Average width | 2.70 cm | 2.31 cm |

Table 3 shows plant characteristics of the new variety compared with plant characteristics of the commercial variety 'Heritage'. Plant characteristics include plant height, diameter, number of crowns per plant, habit, density of individual plant and vigor.

TABLE 3

| Characteristic | 'DrisRaspOne' | 'Heritage' |
|---|---|---|
| Plant size | Large | Medium |
| New cane habit | Erect | Erect |
| Plant productivity | High | Low |
| Self-fruitfulness | Self-fruitful | Self-fruitful |
| Time of bud burst | Late | Early |

Table 4 shows primocane characteristics of the new cultivar compared with primocane characteristics of 'Heritage'. Cane characteristics include primocane fruiting cane length at end of first growing season (cm), fruiting lateral length, length ($4^{th}$ lateral from tip) in centimeters, percent of cane length flowering as primocane, number of young shoots, very young shoots intensity of anthocyanin coloration, time of young shoot emergence from soil, new cane strength (observed full grown shoot after picking), primocane length (cm), glaucosity (waxy bloom)(observed on full grown shoot after picking), cane cross section (form mid cane of primocane observed at end of first growing season), dormant cane color, and internodal distance (cm) (at central ⅓ of cane).

TABLE 4

| Characteristic | 'DrisRaspOne' | 'Heritage' |
|---|---|---|
| Primocane fruiting: cane length at end of first growing season | 219 cm | 204 cm |
| Fruiting lateral length | Medium | Long |
| Length ($4^{th}$ lateral from tip) (cm) | 59.9 | 77.9 |
| Percent of cane length flowering as Primocane | 27% | 28% |
| Percent total yield | 25% | 47% |
| Number of fruit per lateral | Range: 14 to 29 Average: 22.0 | Range: 10 to 40 Average: 21.2 |
| Number of young shoots | Medium | Medium |

TABLE 4-continued

| Characteristic | 'DrisRaspOne' | 'Heritage' |
|---|---|---|
| Very young shoots intensity of anthocyanin coloration | Absent | Weak |
| Time of young shoot emergence from soil | Early | Early |
| New cane strength (observed full grown shoot after picking) | Strong | Strong |
| Glaucosity (waxy bloom)(observed on full grown shoot after picking) | Weak | Medium |
| Cane cross section (form mid-cane of primocane observed at end of first growing season) | Rounded to angular | Rounded to angular |
| Dormant cane color | RHS 164B (Brown) | RHS 166C (Brown to purple) |
| Internodal distance (at central ⅓ of cane) | Range: 3.5 to 5.5 cm Average: 4.6 cm | Range: 3.0 to 6.5 cm Average: 4.1 cm |

Table 5 shows information about the prickles of the new cultivar compared to 'Heritage'. This includes prickles on young shoots, density of spines on central third, attitude of tip, size on young shoots, length in centimeters (mean average of 20 measured 1 meter from ground at end of growing season — base of tip), texture, presence and distribution on petioles, pubescence on canes and color of spines.

TABLE 5

| Characteristic | 'DrisRaspOne' | 'Heritage' |
|---|---|---|
| Prickles: on young shoots | Present | Present |
| Prickles: Density of spines on central third | Medium | Medium |
| Prickles: Attitude of tip | Horizontal | Downward |
| Prickles: Size on young shoots | Small | Medium |
| Prickles: length (mean average of 20 measured 1 meter from ground at end of growing season - base of tip) | 0.16 cm | 0.22 cm |
| Prickles: Texture | Soft | Heavy |
| Presence and distribution on petioles | Present and regularly distributed | Present and regularly distributed |
| Pubescence on canes | Absent | Absent |
| Color of spines | RHS 187A (Brown-purple) | RHS 182A (Purple) |

Table 6 shows information about the leaf and petiole, of the new cultivar compared to 'Heritage'. This includes leaf upper surface color, leaf lower surface color, color relief between veins, glossiness, petiole length in centimeters, petiole pigmentation of upper surface, petiole pigmentation of lower surface.

TABLE 6

| Leaf Characteristic | 'DrisRaspOne' | 'Heritage' |
|---|---|---|
| Leaf upper surface color | RHS 147A (Dark yellow-green) | RHS 147A (Dark yellow-green) |
| Leaf lower surface color | RHS 147C (Medium yellow-green) | RHS 147C (Medium yellow-green) |
| Color relief between veins | Medium | Medium |
| Glossiness | Dark | Medium |

TABLE 6-continued

| Leaf Characteristic | 'DrisRaspOne' | 'Heritage' |
|---|---|---|
| Petiole length | Range: 4.5 to 7.5 cm<br>Average: 6.0 cm | Range: 6.0 to 9.5 cm<br>Average: 7.3 cm |
| Petiole pigmentation of upper surface | RHS 144C<br>(Light yellow-green) | RHS 183C<br>(Dark greyed-purple) |
| Petiole pigmentation lower surface | RHS 144D<br>(Light yellow-green) | RHS 144C<br>(Light yellow-green) |
| Stipule orientation | Clasping | Erect |
| Leaf arrangement | Compound-Alternate<br>(1 leaf per node) | Compound-Alternate<br>(1 leaf per node) |
| Number of leaflets | Usually 5, transitional | Sometimes 3, sometimes 5 |

Table 7 shows information about the terminal leaflet of the new cultivar compared to 'Heritage'. This includes terminal leaflet length in centimeters, terminal leaflet width in centimeters, terminal leaflet shape, terminal leaflet tip, terminal leaflet base, terminal leaflet apex, terminal leaflet shape of teeth, terminal leaflet margin and terminal leaflet cross-section.

TABLE 7

| Characteristic | 'DrisRaspOne' | 'Heritage' |
|---|---|---|
| Terminal leaflet length | 10.3 cm | 14.7 cm |
| Terminal leaflet width | 7.3 cm | 8.3 cm |
| Terminal leaflet shape | Ovate | Ovate |
| Terminal leaflet tip | Acuminate | Acuminate |
| Terminal leaflet base | Cordate | Cordate |
| Terminal leaflet apex | Truncate | Truncate |
| Terminal leaflet shape of teeth | Obtuse | Obtuse |
| Terminal leaflet margin | Doubly serrate | Doubly serrate |
| Terminal leaflet cross-section | Convex | Flat (plane) |

Table 8 shows information about the lateral leaflets of the new cultivar compared to 'Heritage'. This includes overlapping of lateral leaflets, lateral leaflet length to stalklet (lower pair), Lateral leaflet (basal pair), average length of the lateral leaflet in centimeters, average width of the lateral leaflet in centimeters, shape, tip, base, margin and rachis length between terminal leaflet and adjacent lateral leaflet in centimeters.

TABLE 8

| Characteristic | 'DrisRaspOne' | 'Heritage' |
|---|---|---|
| Overlapping of lateral leaflets | Overlapping | Touching |
| Lateral leaflet: length to stalklet (basal pair) | Medium | Short |
| Lateral leaflet average length | 9.6 cm | 13.4 cm |
| Lateral leaflet average width | 6.1 cm | 7.8 cm |
| Lateral leaflet shape | Ovate | Ovate |
| Lateral leaflet tip | Acuminate | Acuminate |
| Lateral leaflet base | Ovate | Ovate |
| Lateral leaflet margin | Doubly serrate | Doubly serrate |
| Lateral leaflet rachis length between terminal leaflet and adjacent lateral leaflet | Range: 3.5 to 5.0 cm<br>Average: 4.1 cm | Range: 3.8 to 6.4 cm<br>Average: 4.9 cm |

Table 9 shows inflorescence characteristics of the new cultivar compared to 'Heritage'. These characteristics include flowering period for the primocane and floricane, flower size, flower length in centimeters, flower width in centimeters, flower number (at 3$^{rd}$ node from tip of lateral), diameter of calyx relative to corolla, spacing of petals (observe only on secondary flowers with 5 to 6 petals), petal length in centimeters, petal width in centimeters, petal shape, petal apex, petal margin, petal base, petal length to width ratio, sepal margin, pedicel anthocyanin coloration and pedicel length.

TABLE 9

| Characteristic | 'DrisRaspOne' | 'Heritage' |
|---|---|---|
| Flowering period: Primocane | Very late | Late |
| Flowering period: Floricane | Very late | Late |
| Flower size | Medium | Small |
| Flower length | 3.5 cm | 3.0 cm |
| Flower width | 3.5 cm | 3.0 cm |
| Flower number (at 3$^{rd}$ node from tip of lateral) | Range: 7 to 16<br>Mean: 9.8 | Range: 6 to 13<br>Mean: 8.7 |
| Diameter of calyx relative to corolla | Smaller | Smaller |
| Spacing of petals (observed on secondary flowers with 5 or 6 petals) | Free | Free |
| Petal length | 8.6 cm | 8.1 cm |
| Petal width | 3.9 cm | 3.7 cm |
| Petal shape | Oval | Oval |
| Petal apex | Rounded | Rounded |
| Petal margin | Entire | Entire |
| Petal base | Convex | Convex |
| Petal length to width ratio | Much longer than broader | Much longer than broader |
| Sepal margin | Entire | Entire |
| Pedicel anthocyanin coloration | Absent | Weak |
| Pedicel length | Medium | Short |

Table 10 shows fruit characteristics of the new cultivar compared to 'Heritage'. These characteristics include harvest season ripening time, length of harvest season, Time of floricane ripening, length of harvest season for floricane, fruit color when immature, fruit color when maturing, fruit color when mature, glossiness of the fruit, shape, size, average length in centimeters, average width in centimeters, ratio of length to width, weight of the primocane, weight of the floricane, soluble solids percentage in Brix, titratable acidity percentage as citric acid, seed weight (g/seed), number of druplets per fruit, adherence to plug, firmness and yield.

TABLE 10

| Characteristic | 'DrisRaspOne' | 'Heritage' |
|---|---|---|
| Harvest season-ripening time | Late July to early November | Early July to early November |
| Length of harvest season | Long | Short |
| Time of ripening-Floricane | Early June to early August | Late May to late July |
| Length of harvest season-Floricane | Medium | Short |
| Fruit color | Medium red | Dark red |
| Fruit color: Immature | RHS 43A<br>(Medium bright red) | RHS 47A<br>(Dark red) |
| Fruit color: Maturing | RHS 45A<br>(Medium red) | RHS 46A<br>(Dark red) |
| Fruit color: Mature fruit | RHS 46A<br>(Dark red) | RHS 185A<br>(Dark greyed-purple) |
| Glossiness | Strong | Medium |
| Shape | Ovate | Ovate |
| Size | Medium | Small |
| Average length | 2.94 cm | 2.26 cm |
| Average width | 2.70 cm | 2.31 cm |
| Ratio of length to width | Longer than broad | As long as broad |
| Weight-Primocane | 4.78 g | 2.96 g |
| Weight-Floricane | 4.50 g | 3.00 g |

TABLE 10-continued

| Characteristic | 'DrisRaspOne' | 'Heritage' |
|---|---|---|
| Soluble solids (%) (in Brix) | 11.1 | 10.3 |
| Titratable acidity (% as citric acid) | 15.3 | 14.4 |
| Seed weight (g/Seed) | 2.84 | 2.25 |
| Number of druplets/fruit | 101 | 102 |
| Adherence to plug | Easy | Easy |
| Firmness | Medium | Medium |
| Yield | High | Low |

We claim:

1. A new and distinct cultivar of raspberry plant as described and shown herein.

* * * * *